United States Patent
Snyder et al.

(10) Patent No.: US 6,927,196 B2
(45) Date of Patent: Aug. 9, 2005

(54) TRANSPARENT CONCENTRATED HAIR CONDITIONING COMPOSITION

(75) Inventors: Michael Albert Snyder, Mason, OH (US); Natsumi Komure, Ashiya (JP)

(73) Assignee: The Procter & Gamble Company, Cincinnati, OH (US)

( * ) Notice: Subject to any disclaimer, the term of this patent is extended or adjusted under 35 U.S.C. 154(b) by 26 days.

(21) Appl. No.: 10/387,885

(22) Filed: Mar. 13, 2003

(65) Prior Publication Data

US 2003/0216267 A1 Nov. 20, 2003

Related U.S. Application Data

(63) Continuation of application No. PCT/US01/28475, filed on Sep. 13, 2001.

(51) Int. Cl.$^7$ .............................. C11D 1/62; C11D 9/36
(52) U.S. Cl. ..................... 510/124; 510/119; 510/122; 510/123; 510/466; 510/504
(58) Field of Search ................................ 510/119, 122, 510/123, 466, 504, 124

(56) References Cited

U.S. PATENT DOCUMENTS

| | | | |
|---|---|---|---|
| 4,559,227 A | * 12/1985 | Chandra et al. | ............. 510/122 |
| 4,954,335 A | * 9/1990 | Janchipraponvej | ....... 424/70.28 |
| 4,978,526 A | 12/1990 | Gesslein et al. | |
| 5,145,607 A | * 9/1992 | Rich | ........................ 510/122 |
| 5,244,598 A | * 9/1993 | Merrifield et al. | ............. 516/55 |
| 5,286,476 A | * 2/1994 | Nanba et al. | .................. 424/47 |
| 5,518,716 A | 5/1996 | Riccio et al. | |
| 5,641,480 A | 6/1997 | Vermeer | |
| 5,679,331 A | * 10/1997 | Hague et al. | ............. 424/70.19 |
| 6,048,520 A | * 4/2000 | Hoshowski | ............... 424/70.17 |
| 6,147,038 A | * 11/2000 | Halloran | ..................... 510/122 |

FOREIGN PATENT DOCUMENTS

| | | |
|---|---|---|
| JP | 07 215828 A | 8/1995 |
| WO | WO-96/29980 A1 | 10/1996 |
| WO | WO-99/13823 A2 | 3/1999 |
| WO | WO-01/97761 A1 | 12/2001 |

* cited by examiner

*Primary Examiner*—Charles Boyer
(74) *Attorney, Agent, or Firm*—Linda M. Sivik; Tara M. Rosnell

(57) ABSTRACT

Disclosed is a transparent concentrated hair conditioning composition comprising:
(1) from about 0.01% to about 50% by weight of a conditioning agent selected from the group consisting of cationic surfactants, cationic polymers, silicone compounds, polyalkylene glycols, and mixtures thereof; and
(2) an aqueous carrier;
(3) wherein the hair conditioning composition is used for conditioning the hair comprising the steps of;
   (a) applying a shampoo composition comprising a detersive surfactant to the hair;
   (b) providing a treated water by dispersing the conditioning composition to water, wherein the treated water has a concentration by weight of from 0.001% to 2% of the conditioning agent; and
   (c) rinsing the hair with the treated water;
   and wherein steps (a) and (b) may be reversed;
(4) wherein the conditioning composition has a turbidity of no more than about 200 NTU, and the treated water has a turbidity of no more than about 100 NTU.

6 Claims, No Drawings

TRANSPARENT CONCENTRATED HAIR CONDITIONING COMPOSITION

CROSS REFERENCE TO RELATED APPLICATION

The application is a continuation of International application PCT/US01/28475 (Case AA567F) filed on Sep. 13, 2001, which claims priority to International application PCT/US00/24973 (Case M495F) filed on Sep. 13, 2000.

FIELD OF THE INVENTION

The present invention relates to concentrated hair conditioning compositions which are transparent, and which deliver hair conditioning benefit to the hair by dispersing the composition to the rinse water and rinsing the shampooed hair with such treated rinse water.

BACKGROUND

Human hair becomes soiled due to its contact with the surrounding environment and from the sebum secreted by the scalp. The soiling of hair causes it to have a dirty feel and an unattractive appearance. The soiling of the hair necessitates shampooing with frequent regularity.

Shampooing cleans the hair by removing excess soil and sebum. However, shampooing can leave the hair in a wet, tangled, and generally unmanageable state. Once the hair dries, it is often left in a dry, rough, lusterless, or frizzy condition due to removal of the hairs natural oils and other natural hair conditioning and moisturizing components. The hair can further be left with increased levels of static upon drying, which can interfere with combing and result in a condition commonly referred to as "fly-away hair", or contribute to an undesirable phenomena of "split ends", particularly for long hair.

A variety of approaches have been developed to alleviate these after-shampoo problems. These approaches range from post-shampoo application of hair conditioners such as leave-on and rinse-off products, to hair conditioning shampoos which attempt to both clean and condition the hair from a single product.

Although some consumers prefer the ease and convenience of a shampoo which includes conditioners, a substantial proportion of consumers prefer the more conventional conditioner formulations which are applied to the hair as a separate step from shampooing, usually subsequent to shampooing. The conditioning formulations thus applied to the hair would then typically be rinsed off from the hair, and the hair would be left to dry.

In order to meet the needs of consumers living in locations where water supply is unstable and thereby desiring conditioning benefit to the hair without using water excess to the amount that would be used for shampooing the hair, a concentrated hair conditioning composition and its method of use was proposed in co-pending PCT application PCT/US00/24973. Such concentrated hair conditioning composition is used by (a) applying a shampoo composition comprising a detersive surfactant to the hair; (b) providing a treated water made by dispersing the concentrated hair conditioning composition to water in, for example, a basin and/or scoop; and (c) rinsing the hair with the treated water; wherein steps (a) and (b) may be reversed. In view of such method of use, good dispersing properties upon contact with water is desired for concentrated hair conditioning compositions. Further, in that consumers tend to associate good dispersing properties by the transparent appearance of the obtained treated water, a concentrated hair conditioning composition having a transparent appearance by itself and are capable of providing transparent treated water is desired. Still further, consumers do not wish to compromise on conditioning performance for such transparent appearance.

Based on the foregoing, there remains a desire to provide concentrated hair conditioning compositions which have a transparent appearance by itself and are capable of providing transparent treated water. There is also a desire to provide such conditioning compositions which disperse easily upon contact with water, yet provide hair conditioning benefits such as smooth feel when the hair is wet, combing ease when the hair is wet or dry, and softness when the hair is dry.

None of the existing art provides all of the advantages and benefits of the present invention.

SUMMARY

The present invention is directed to a transparent concentrated hair conditioning composition comprising:

(1) from about 0.01% to about 50% by weight of a conditioning agent selected from the group consisting of cationic surfactants, cationic polymers, silicone compounds, polyalkylene glycols, and mixtures thereof; and (2) an aqueous carrier;

(3) wherein the hair conditioning composition is used for conditioning the hair comprising the steps of;

(a) applying a shampoo composition comprising a detersive surfactant to the hair;

(b) providing a treated water by dispersing the conditioning composition to water, wherein the treated water has a concentration by weight of from 0.001% to 2% of the conditioning agent; and (c) rinsing the hair with the treated water;

and wherein steps (a) and (b) may be reversed;

(4) wherein the conditioning composition has a turbidity of no more than about 200 NTU, and the treated water has a turbidity of no more than about 100 NTU.

These and other features, aspects, and advantages of the present invention will become evident to those skilled in the art from a reading of the present disclosure.

Definitions

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "treated water" means the water to which the conditioning agent of the concentrated hair conditioning composition of the present invention is dispersed, the treated water having a concentration of 0.001% to 2% of the conditioning agent.

Herein, "dispersible" with regard to the conditioning composition, silicone conditioning agent, or additional conditioning agent, means being capable of providing homogenous treated water when released in water and mixed by hand for no more than 30 seconds, and "dispersability" means such ability.

Herein, "transparent" with regard to the conditioning composition, prior to dispersing in water, means having a turbidity of no more than about 200 NTU (Nephelometric Turbidity Units). Herein, "transparent" with regard to the treated water means being homogeneous, and having a turbidity of no more than about 100 NTU. The NTU values are measured using the Hach 2100N Laboratory Turbidimeter calibrated with Formazin standards, available from Hach Company. Herein, "deposition" means the weight ratio (ppm) of a silicone conditioning agent deposited on a hair sample calculated according to the following: Measurement is made by immersing a measured weight of hair in a treated water containing a measured concentration of the silicone conditioning agent, wherein such concentration is controlled to be between 0.001% to 2%; and analyzing such treated hair for silicon content as a surrogate for the silicone conditioning agent via Inductively Coupled Plasma—Atomic Emission Spectroscopy (ICP-AES); The ICP-AES analysis is conducted using the SPS4000 system available from Seiko Corporation. A response factor obtained by measuring the standard silicone conditioning agent solution is introduced.

DETAILED DESCRIPTION

While the specification concludes with claims which particularly point out and distinctly claim the invention, it is believed the present invention will be better understood from the following description.

All cited references are incorporated herein by reference in their entireties. Citation of any reference is not an admission regarding any determination as to its availability as prior art to the claimed invention.

Method of Conditioning and Product Form

The present invention is directed to a concentrated hair conditioning composition which is used by a method comprising the steps of:

(a) applying a shampoo composition comprising a detersive surfactant to the hair;
(b) providing a treated water made by dispersing the conditioning composition to water, wherein the treated water has a concentration by weight of from 0.001% to 2% of the conditioning agent of the conditioning composition; and
(c) rinsing the hair with the treated water.

Steps (a) and (b) may be reversed. In the method of the present invention, the hair conditioning composition is dispersed in water, and the treated water thus obtained is applied to the hair. The term "treated water" is defined under the Definitions Section above. This term as used herein describes water provided by the user and to which at least the conditioning composition is dispersed, and in addition, optionally other components such as rinse aid systems are dispersed in the same water. Such treated water is applied to the hair after a shampoo composition comprising a detersive surfactant is applied and worked through the hair. Thus, rinsing the hair with treated water provides two functions at the same time, namely, it washes away the shampoo composition and soils from the hair while also providing conditioning benefit to the hair. This allows the user to provide conditioning benefits to the hair without using water excess to the amount that would be used for shampooing the hair. The treated water can be made in a basin and/or scoop, or any other convenient vessel, typically a basin and/or scoop available in the user's home. When more than one basins or scoops of water are used to rinse the hair, the conditioning composition can be added to any or all basins or scoops to be used for rinsing the hair. Preferably, the treated water is prepared for the basin or scoop to be used last.

The shampoo composition to be used in step (a) can be any composition comprising detersive surfactants and is suitable for washing off soils from the hair. The term detersive surfactant, as used herein, is intended to distinguish these surfactants from surfactants which are primarily emulsifying surfactants, i.e. surfactants which provide an emulsifying benefit and which have low cleansing performance. It is recognized that most surfactants have both detersive and emulsifying properties. It is not intended to exclude emulsifying surfactants from the present invention, provided the surfactant also possesses sufficient detersive properties to be useful herein. Detersive surfactants are typically selected from the group consisting of anionic surfactants, amphoteric surfactants, nonionic surfactants, and mixtures thereof. In one preferred embodiment, at least an anionic surfactant is included in the shampoo composition to be used in step (a), and a cationic conditioning agent is included in the conditioning composition to be used in step (c).

The present invention is also directed to a method of purifying water for applying to the hair; such method comprising the step of adding a rinse aid system to the water. The term "purified water" as used herein describes water provided by the user and to which the rinse aid system is dispersed in the water. It has been surprisingly found that, when the pre-purified water contains a high amount of heavy metal ions and salts, the purified water obtained by the method herein can provide benefit to the hair when applied, such as soft feel to the hair, even without conditioning agents, as compared to the pre-purified water. The rinse aid system for purifying water is preferably included in the concentrated hair conditioning composition.

For providing a conditioning benefit to the hair while not negatively affecting the rinsing ability of the shampoo composition and soils from the hair, the treated water has a concentration by weight of from 0.001% to 2%, preferably from about 0.005% to about 0.5% of conditioning agent. In order for the user to achieve this suitable concentration of treated water, the conditioning composition of the present invention may be provided in a package means containing a unit dose of the conditioning composition, or with a measuring means. The dosage of the composition is determined based on the amount of water contained in an average size vessel provided by the user, for example a basin and/or scoop, for making the treated water.

The conditioning composition of the present invention can be provided in any form which is suitable for transportation and storage at ambient temperatures, and is readily applicable to the water upon use to make the treated water. As the conditioning composition is designed to readily disperse in water, the composition is typically easily degraded by humidity. Packaging for any product form is selected to avoid humidity and preferably, accidental contact with water.

The conditioning composition of the present invention is in the form of a liquid such as a gel or paste, the carrier being aqueous. Suitable packaging for such product form include sachets, or constructed packaging having one or more compartments.

Conditioning Agent

The conditioning agents useful in the present invention are those which are dispersible in water, provide a transparent concentrated hair conditioning composition, and provide a transparent treated water. The terms "dispersible" and "transparent" are defined in the Definitions Section above. Suitable conditioning agents are selected from the group consisting of cationic surfactants, cationic polymers, silicone compounds, polyalkylene glycols and mixtures thereof, preferably mono long-chain ammonium compounds, hydrophilically substituted cationic surfactants, cationic polymers, hydrophilically substituted silicone compounds, polyalkylene glycols, and mixtures thereof. The type of conditioning agents are selected depending on the desired characteristics of the product. Highly water soluble conditioning agents are typically used. A combination of conditioning agents is preferably used to provide benefits provided by the different conditioning agents. Conditioning agents which are less water soluble can be used in combination with highly water soluble conditioning agents.

The present composition comprises from about 0.01% to about 50%, preferably from about 1% to about 20% of conditioning agents. The level is selected according to the form in which the product is provided and to the desired concentration of the treated water to be made and applied to the hair.

In one embodiment, the conditioning composition of the present invention comprises from about 1% to about 10% of a mono long-chain ammonium compound or a hydrophilically substituted cationic surfactant and from about 1% to about 10% of a cationic polymer.

Cationic Surfactant

Cationic surfactants are useful as conditioning agents herein. Among the cationic surfactants useful herein are those generally described as mono long-chain ammonium compounds, corresponding to the general formula (I):

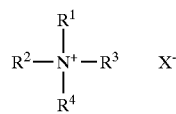

wherein $R^1$ is selected from an aliphatic group of from 8 to 30 carbon atoms or an aromatic, alkoxy, polyoxyalkylene, alkylamido, hydroxyalkyl, aryl or alkylaryl group having up to about 22 carbon atoms, $R^2$, $R^3$, and $R^4$ are independently selected from an aliphatic group of from 1 to about 3 carbon atoms or an aromatic, alkoxy, polyoxyalkylene, alkylamido, hydroxyalkyl, aryl or alkylaryl group having up to about 8 carbon atoms; and X is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The aliphatic groups can contain, in addition to carbon and hydrogen atoms, ether linkages, and other groups such as amino groups. The longer chain aliphatic groups, e.g., those of about 12 carbons, or higher, can be saturated or unsaturated. Preferred is when $R^1$ is selected from $C_8$ to about $C_{22}$ alkyl.

Among the cationic surfactants of general formula (I), preferred are those containing in the molecule at least one alkyl chain having at least 16 carbons. Nonlimiting examples of such preferred cationic surfactants include: cetyl trimethyl ammonium chloride available, for example, with tradename CA-2350 from Nikko Chemicals and CTAC 30KC available from KCI, stearyl trimethyl ammonium chloride with tradename Arquad 18/50 available from Akzo Nobel, hydrogenated tallow alkyl trimethyl ammonium chloride, stearyl dimethyl benzyl ammonium chloride, stearyl propyleneglycol phosphate dimethyl ammonium chloride, stearoyl amidopropyl dimethyl benzyl ammonium chloride, stearoyl amidopropyl dimethyl (myristylacetate) ammonium chloride, and N-(stearoyl colamino formyl methy) pyridinium chloride.

Also preferred are hydrophilically substituted cationic surfactants in which at least one of the substituents contain one or more aromatic, ether, ester, amido, or amino moieties present as substituents or as linkages in the radical chain, wherein at least one of the $R^1$–$R^4$ radicals contain one or more hydrophilic moieties selected from alkoxy (preferably $C_1$–$C_3$ alkoxy), polyoxyalkylene (preferably $C_1$–$C_3$ polyoxyalkylene), alkylamido, hydroxyalkyl, alkylester, and combinations thereof. Preferably, the hydrophilically substituted cationic conditioning surfactant contains from 2 to about 10 nonionic hydrophile moieties located within the above stated ranges. Preferred hydrophilically substituted cationic surfactants include those of the formula (II) through (VIII) below:

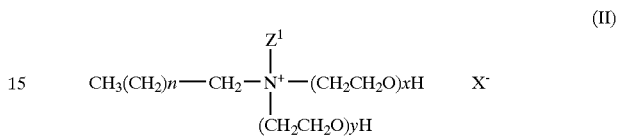

wherein n is from 8 to about 28, x+y is from 2 to about 40, $Z^1$ is a short chain alkyl, preferably a $C_1$–$C_3$ alkyl, more preferably methyl, or $(CH_2CH_2O)_zH$ wherein x+y+z is up to 60, and X is a salt forming anion as defined above;

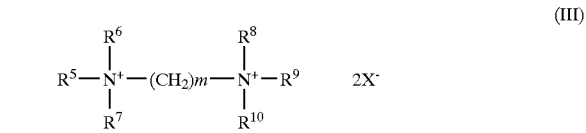

wherein m is 1 to 5, one or more of $R^5$, $R^6$, and $R^7$ are independently an $C_1$–$C_{30}$ alkyl, the remainder are $CH_2CH_2OH$, one or more of $R^8$, $R^9$, and $R^{10}$ are independently an $C_1$–$C_{30}$ alkyl, and remainder are $CH_2CH_2OH$, and X is a salt forming anion as mentioned above;

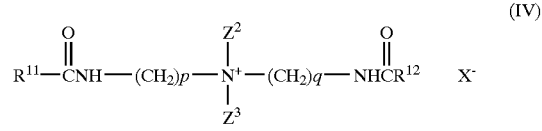

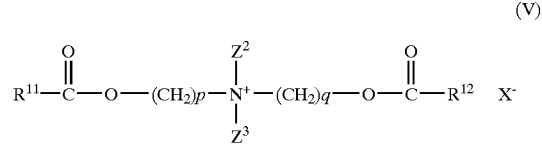

wherein, independently for formulae (IV) and (V), $Z^2$ is an alkyl, preferably a $C_1$–$C_3$ alkyl, more preferably methyl, and $Z^3$ is a short chain hydroxyalkyl, preferably hydroxymethyl or hydroxyethyl, p and q independently are integers from 2 to 4, inclusive, preferably from 2 to 3, inclusive, more preferably 2, $R^{11}$ and $R^{12}$, independently, are substituted or unsubstituted hydrocarbyls, preferably $C_{12}$–$C_{20}$ alkyl or alkenyl, and X is a salt forming anion as defined above;

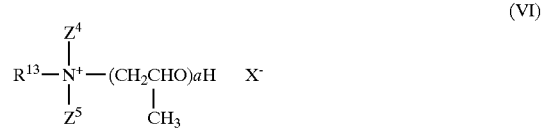

wherein $R^{13}$ is a hydrocarbyl, preferably a $C_1$–$C_3$ alkyl, more preferably methyl, $Z^4$ and $Z^5$ are, independently, short chain hydrocarbyls, preferably $C_2$–$C_4$ alkyl or alkenyl, more preferably ethyl, a is from 2 to about 40, preferably from about 7 to about 30, and X is a salt forming anion as defined above;

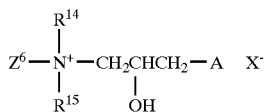
(VII)

wherein $R^{14}$ and $R^{15}$, independently, are $C_1$–$C_3$ alkyl, preferably methyl, $Z^6$ is a $C_{12}$–$C_{22}$ hydrocarbyl, alkyl carboxy or alkylamido, and A is a protein, preferably a collagen, keratin, milk protein, silk, soy protein, wheat protein, or hydrolyzed forms thereof; and X is a salt forming anion as defined above;

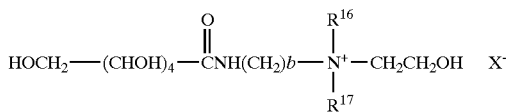
(VIII)

wherein b is 2 or 3, $R^{16}$ and $R^{17}$, independently are $C_1$–$C_3$ hydrocarbyls preferably methyl, and X is a salt forming anion as defined above. Nonlimiting examples of hydrophilically substituted cationic surfactants useful in the present invention include the materials having the following CTFA designations: quaternium-16, quaternium-26, quaternium-27, quaternium-30, quaternium-33, quaternium-43, quaternium-52, quaternium-53, quaternium-56, quaternium-60, quaternium-61, quaternium-62, quaternium-70, quaternium-71, quaternium-72, quaternium-75, quaternium-76 hydrolyzed collagen, quaternium-77, quaternium-78, quaternium-79 hydrolyzed collagen, quaternium-79 hydrolyzed keratin, quaternium-79 hydrolyzed milk protein, quaternium-79 hydrolyzed silk, quaternium-79 hydrolyzed soy protein, and quaternium-79 hydrolyzed wheat protein, quaternium-80, quaternium-81, quaternium-82, quaternium-83, quaternium-84, and mixtures thereof.

Highly preferred hydrophilically substituted cationic surfactants include dialkylamido ethyl hydroxyethylmonium salt, dialkylaminoethyl dimonium salt, dialkyloyl ethyl hydroxyethylmonium salt, dialkyloyl ethyldimonium salt, alkyl amidopropyl trimonium salt, polyoxyethylene alkyl ammonium salt, and mixtures thereof; for example, commercially available under the following tradenames; VARISOFT 110, VARISOFT PATC, VARIQUAT K1215 and 638 from Witco Chemical, ETHOQUAD 18/25, ETHOQUAD O/12PG, ETHOQUAD C/25, and ETHOQUAD S/25 from Akzo, DEHYQUART SP from Henkel, and MONAQUAT ISEIS, and MONAQUAT SL-5 available from Uniqema.

Cationic Polymer

Cationic polymers are useful as conditioning agents herein. As used herein, the term "polymer" shall include materials whether made by polymerization of one type of monomer or made by two (i.e., copolymers) or more types of monomers.

The cationic polymers hereof will generally have a weight average molecular weight which is at least about 5,000, typically at least about 10,000, and is less than about 10 million. Preferably, the molecular weight is from about 100,000 to about 2 million. The cationic polymers will generally have cationic nitrogen-containing moieties such as quaternary ammonium or cationic amino moieties, and mixtures thereof.

Any anionic counterions can be utilized for the cationic polymers so long as the water solubility criteria is met. Suitable counterions include halides (e.g., Cl, Br, I, or F, preferably Cl, Br, or I), sulfate, and methylsulfate. Others can also be used, as this list is not exclusive.

The cationic nitrogen-containing moiety will be present generally as a substituent, on a fraction of the total monomer units of the cationic polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in the CTFA Cosmetic Ingredient Dictionary, 3rd edition, edited by Estrin, Crosley, and Haynes, (The Cosmetic, Toiletry, and Fragrance Association, Inc., Washington, D.C., 1982).

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the composition. In general, secondary and tertiary amines, especially tertiary amines, are preferred.

Amine-substituted vinyl monomers can be polymerized in the amine form, and then optionally can be converted to ammonium by a quaternization reaction. Amines can also be similarly quaternized subsequent to formation of the polymer. For example, tertiary amine functionalities can be quaternized by reaction with a salt of the formula R'X wherein R' is a short chain alkyl, preferably a $C_1$–$C_7$ alkyl, more preferably a $C_1$–$C_3$ alkyl, and X is an anion which forms a water soluble salt with the quaternized ammonium.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, dialyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$–$C_3$ alkyls, more preferably $C_1$ and $C_2$ alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

The cationic polymers hereof can comprise mixtures of monomer units derived from amine- and/or quaternary ammonium-substituted monomer and/or compatible spacer monomers.

Suitable cationic hair conditioning polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7 such as those with tradenames Salcare SC10 and Salcare SC11 available from Ciba Specialty Chemicals, and those commercially available from Calgon with tradename Merquat 2200, respectively; and mineral acid salts of amino-alkyl esters of homo- and co-polymers of unsaturated carboxylic acids having from 3 to 5 carbon atoms, as described in U.S. Pat. No. 4,009,256, incorporated herein by reference.

Other cationic polymers that can be used include polysaccharide polymers, such as cationic cellulose derivatives and cationic starch derivatives.

Cationic polysaccharide polymer materials suitable for use herein include those of the formula:

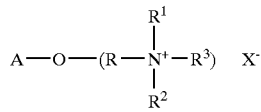

wherein: A is an anhydroglucose residual group, such as a starch or cellulose anhydroglucose residual, R is an alkylene oxyalkylene, polyoxyalkylene, or hydroxyalkylene group, or combination thereof, $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less, and X is an anionic counterion, as previously described.

Highly preferred cationic cellulose polymers are available from Amerchol Corp. (Edison, N.J., USA) in their Polymer JR® and LR® series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Quaterisoft Polymer LM-®.

Other cationic polymers that can be used include cationic guar gum derivatives, such as guar hydroxypropyltrimonium chloride (commercially available from Celanese Corp. in their Jaguar R series). Other materials include quaternary nitrogen-containing cellulose ethers (e.g., as described in U.S. Pat. No. 3,962,418, incorporated herein by reference), and copolymers of etherified cellulose and starch (e.g., as described in U.S. Pat. No. 3,958,581, incorporated herein by reference.)

Other cationic polymers useful herein are:
(1) Cationic polymers chosen from the group comprising:
i) polymers containing units of the formula:

$$—A—Z^1—A—Z^2 \quad\quad (I)$$

wherein A denotes a radical containing two amino groups, preferably a piperazinyl radical, and $Z^1$ and $Z^2$ independently denote a divalent radical which is a straight-chain or branched-chain alkylene radical which contains up to about 7 carbon atoms in the main chain, is unsubstituted or substituted by one or more hydroxyl groups and can also contain one or more oxygen, nitrogen and sulphur atoms and 1 to 3 aromatic and/or heterocyclic rings, the oxygen, nitrogen and sulphur atoms generally being present in the form of an ether or thioether, sulphoxide, sulphone, sulphonium, amine, alkylamine, alkenylamine, benzylamine, amine oxide, quaternary ammonium, amide, imide, alcohol, ester and/or urethane group;

ii) polymers containing units of the formula:

$$—A—Z'—A—Z' \quad\quad (II)$$

wherein A denotes a radical containing two amino groups, preferably a piperazinyl radical, and Z' denotes the symbol $Z^3$ and $Z^4$ while denoting the symbol $Z^4$ at least once; $Z^3$ denotes a divalent radical which is a straight-chain or branched-chain alkylene or hydroxyalkylene radical having up to about 7 carbon atoms in the main chain, and $Z^4$ is a divalent radical which is a straight-chain or branched-chain alkylene radical which has up to about 7 carbon atoms in the main chain, is unsubstituted and substituted by one or more hydroxyl radicals and is interrupted by one or more nitrogen atoms, the nitrogen atom being substituted by an alkyl chain having from 1 to 4 carbon atoms, preferably 4 carbon atoms, which is optionally interrupted by an oxygen atom and optionally contains one or more hydroxyl groups; and iii) the alkylation products, with alkyl and benzyl halides of 1 to 6 carbon atoms, alkyl tosylates or mesylates, and the oxidation products, of the polymers of the formulae (I) and (II) indicated above under i) and ii).

(2) Polyamino-polyamides prepared by the polycondensation of an acid compound with a polyamine. The acid compound can be organic dicarboxylic acids, aliphatic monocarboxylic and dicarboxylic acids containing a double bond, esters of the abovementioned acids, preferably the esters with lower alkanols having from 1 to 6 carbon atoms, and mixtures thereof. The polyamine is a bis-primary or mono- or bis-secondary polyalkylene-polyamine wherein up to 40 mol % of this polyamine can be a bis-primary amine, preferably ethylenediamine, or a bis-secondary amine, preferably piperazine, and up to 20 mol % can be hexamethylenediamine.

(3) The above mentioned polyamino-polyamides can be alkylated and/or crosslinked. The alkylation can be carried out with glycidol, ethylene oxide, propylene oxide or acrylamide. The crosslinking is carried out by means of a crosslinking agent such as:

i) epihalogenohydrins, diepoxides, dianhydrides, unsaturated anhydrides and bis-saturated derivatives, in proportions of 0.025 to 0.35 mol of crosslinking agent per amine group of the polyamino-polyamide;

ii) bis-halogenohydrins, bis-azetidinium compounds, bishalogeno acyldiamines and bis-(alkyl halides);

iii) oligomers obtained by reacting a compound chosen from the group comprising bis-halogenohydrins, bis-azetidinium compounds, bis-halogenoacyl-diamines, bis-(alkyl halides), epihalogenohydrins, diepoxides and bis-unsaturated derivatives, with another compound which is a difunctional compound which is reactive towards the compound; and iv) the quaternisation product of a compound chosen from the compounds i) and the oligomers iii) and containing one or more tertiary amine groups which can be totally or partially alkylated with an alkylating agent preferably chosen from methyl or ethyl chlorides, bromides, iodides, sulphates, mesylates and tosylates, benzyl chloride or bromide, ethylene oxide, propylene oxide and glycidol, the crosslinking being carried out by means of 0.025 to 0.35 mol, in particular of 0.025 to 0.2 mol and more particularly of 0.025 to 0.1 mol, of crosslinking agent per amine group of the polyamino-polyamide.

(4) Polyamino-polyamide derivatives resulting from the condensation of a polyalkylene-polyamine with a polycarboxylic acid, followed by alkylation by means of difunctional agents, such as the adipic acid/dialkylaminohydroxyalkyl-dialkylenetriamine copolymers in which the alkyl radical contains 1 to 4 carbon atoms and preferably denotes methyl, ethyl or propyl.

Useful polymers are adipic acid/dimethylaminohydroxypropyl-diethylenetriamine copolymers sold under the name Cartaretine F, $F^4$ or $F^8$ by SANDOZ.

(5) Polymers obtained by reacting polyalkylenepolyamine containing two primary amine groups and at least one secondary amine group, with a dicarboxylic acid chosen from diglycolic acid and saturated aliphatic dicarboxylic acids having 3 to 8 carbon atoms, the molar ratio of the polyalkylene-polyamine to the dicarboxylic acid being from 0.8:1 to 1.4:1, and the resulting polyamide being reacted with epichlorohydrin in a molar ratio of epichlorohydrin to the secondary amine groups of the polyamide of from 0.5:1 to 1.8:1.

Useful polymers are those sold under the name HERCOSETT 57 by Hercules Incorporated, and that sold under the name PD 170 or DELSETTE 101 by Hercules.

(6) Cyclic polymers generally having a molecular weight of 20,000 to 3,000,000 such as homopolymers containing, as the main constituent of the chain, units corresponding to the formula (III) or (III')

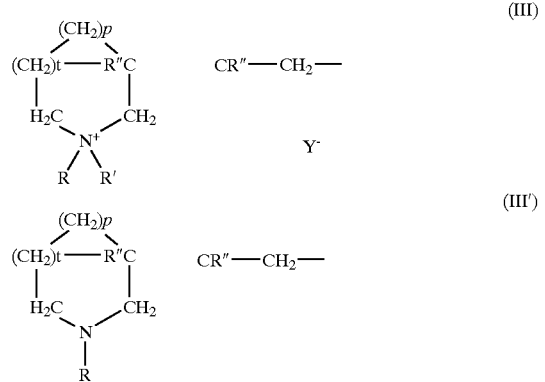

in which p and t are 0 or 1, and p+t=1, R" denotes hydrogen or methyl, R and R' independently of one another denote an alkyl group having from 1 to 22 carbon-atoms, a hydroxylalkyl group in which the alkyl group preferably has 1 to 5 carbon atoms, or a lower amidoalkyl group, and R and R' can denote, together with the nitrogen atom to which they are attached, heterocyclic groups such as piperidinyl or morpholinyl, and Y is bromide, chloride, acetate, borate, citrate, tartrate, bisulphate, bisulphite, sulphate or phosphate. Copolymers containing units of the formula III and III' may also contain units derived from acrylamide or from diacetoneacrylamide.

Amongst the quaternary ammonium polymers of the type defined above, those which are preferred are the dimethyldiallylammonium chloride homopolymer sold under the name MERQUAT 100 and having a molecular weight of less than 100,000, and the dimethyldiallylammonium chloride/acrylamide copolymer having a molecular weight of more than 500,000 and sold under the name MERQUAT 550 by CALGON Corporation.

(7) Poly-(quaternary ammonium) compounds of the formula

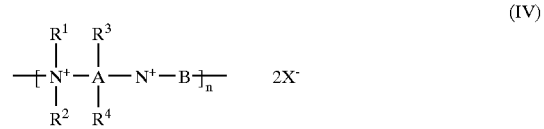

(IV)

wherein $R^1$, $R^2$, $R^3$, and $R^4$ are independently aliphatic, alicyclic or arylaliphatic radicals containing a maximum of 20 carbon atoms, or lower hydroxyaliphatic radicals, or alternatively, with the nitrogen atoms to which they are attached, heterocyclic rings optionally containing a second hetero-atom other than nitrogen, or alternatively $R^1$, $R^2$, $R^3$, and $R^4$ represent a group $CH_2CHR'^3R'^4$ wherein $R'^3$ denoting hydrogen or lower alkyl and $R'^4$ denoting SO, CN, $CON(R'^6)_2$, $COOR'^5$, $COR'^5$, $COOR'^7D$, or $CONHR'^7D$; $R'^5$ denoting lower alkyl, $R'^6$ denoting hydrogen or lower alkyl, $R'^7$ denoting alkylene and D denoting a quaternary ammonium group; A and B independently represent a polymethylene group containing from 2 to 20 carbon atoms, which can be linear or branched, saturated or unsaturated and can contain, inserted in the main chain one or more groups —$CH_2$—Y—$CH_2$— wherein Y denotes benzene, oxygen, sulfur, SO, $SO_2$, SS, $NR'^8$, $N^+(R'^9)_2X^1$—, CHOH, NHCONH, $CONR'^8$, or COO; $X^1$— denoting an anion derived from a mineral or organic acid, $R'^8$ denoting hydrogen or lower alkyl and $R'^9$ denoting lower alkyl, or alternatively A and $R^1$ and $R^3$ form a piperazine ring with the two nitrogen atoms to which they are attached. If A denotes a linear or branched, saturated or unsaturated alkylene or hydroxyalkylene radical, B can also denote a group: —$(CH_2)_n$—CO—D—OC—$(CH_2)_n$—; wherein n is selected so that the molecular weight is generally between 1,000 and 100,000; and D denotes:

i) a glycol radical of the formula —O—Z—O—, in which Z denotes a linear or branched hydrocarbon radical or a group corresponding to the formulae: —[$CH_2$—$CH_2$—O—]$_x$—$CH_2$—$CH_2$— or —[$CH_2$—$C(CH_3)H$—O—]$_y$—$CH_2$—$C(CH_3)H$— wherein x and y denote an integer from 1 to 4, representing a definite and unique degree of polymerisation;

ii) a bis-secondary diamine radical, such as a piperazine derivative;

iii) a bis-primary diamine radical of the formula: —N—H—Y—NH—, in which Y denotes a linear or branched hydrocarbon radical or the divalent radical

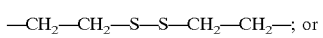

iv) a ureylene group of the formula —N—H—CO—NH—.

(8) Homopolymers or copolymers derived from acrylic or methacrylic acid and containing at least one unit:

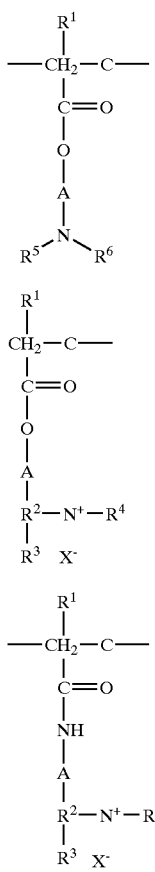

(V)

(V')

(V″)

wherein $R^1$ is H or $CH_3$, A is a linear or branched alkyl group having 1 to 6 carbon atoms or a hydroxyalkyl group having 1 to 4 carbon atoms, $R^2$, $R^3$ and $R^4$ independently denote an alkyl group having 1 to 18 carbon atoms or a benzyl group, $R^5$ and $R^6$ denote H or alkyl having 1 to 6 carbon atoms and X denotes methosulphate or halide, such as chloride or bromide.

The comonomer or comonomers which can be used typically belong to the family comprising: acrylamide, methacrylamide, diacetone-acrylamide, acrylamide and methacrylamide substituted on the nitrogen by one or more lower alkyls, alkyl esters of acrylic and methacrylic acids, vinylpyrrolidone and vinyl esters.

(9) Other cationic polymers which can be used are polyalkyleneimines, in particular polyethyleneimines, polymers containing vinylpyridine units or vinylpyridinium units in the chain, condensates of polyamines and of epichlorohydrin, poly-(quaternary ureylenes) and chitin derivatives.

Highly preferred cationic polymers include commercially available material such as Polyquaternium 4 under the tradenames CELQUAT H100 and CELQUAT L200 supplied by National Starch & Chemicals, Polyquaternium 7 with tradenames Salcare SC10 and Salcare SC11 available from Ciba Specialty Chemicals, and Polyquaternium 11 under the tradename GAFQUAT 755N supplied by ISP.

Silicone Compound

The silicone compounds useful herein include volatile or nonvolatile dispersible silicone compounds having hair conditioning properties. Preferred are hydrophilically substituted silicone compounds. The silicone compounds for use herein will preferably have a viscosity of less than about 5,000 mPa·s at 25° C., more preferably less than about 1,000 mPa·s at 25° C.

The viscosity can be measured by means of a glass capillary viscometer as set forth in Dow Corning Corporate Test Method CTM0004, Jul. 20, 1970. Other nonvolatile silicone compounds having hair conditioning properties can also be used. Without being bound by theory, silicone compounds having lower viscosities are believed to provide faster dispersion when in contact with water.

Particularly preferred silicone compounds herein are those having substitute groups selected from the group consisting of alkoxy groups, amino groups, quaternary amino groups, and mixtures thereof. Silicone compounds having alkoxy groups such as ethylene oxide groups are preferred as they are easily dispersed in water, and provide good transparency to the treated water. Silicone compounds having amino groups and/or quaternary amino groups are preferred as they have good solubility, and also provide good conditioning performance as being substantive to the hair surface.

When silicone compounds having no hydrophilic functionality and/or viscosities of over 5,000 mPa·s at 25° C. are used, they are kept to a small amount, as they tend to make the treated water turbid, or make the composition less dispersible. It is known that transparent compositions containing silicone compounds of high molecular weight can be made by utilizing available emulsion techniques. However, the emulsion structure of such transparent compositions including silicone compounds of high molecular may be destroyed upon dispersion in an abundant amount of water, i.e., upon making the treated water.

In one embodiment, the composition of the present invention comprises from about 0.01% to about 20% of a hydrophilically substituted silicone compound having substitute groups selected from the group consisting of alkoxy groups, amino groups, quaternary groups, and mixtures thereof.

In one embodiment, the composition of the present invention comprises a silicone compound that provide a deposition of from about 10 ppm to about 5000 ppm, when applied to the hair as the treated water. The term "deposition" is defined in the Definitions Section above.

The hydrophilically substituted silicone conditioning agents that can be used include, for example, a polyethylene oxide modified polydimethylsiloxane although mixtures of ethylene oxide and propylene oxide can also be used. The polypropylene oxide level should be sufficiently low so as not to interfere with the dispersability characteristics of the silicone. These materials are also known as dimethicone copolyols. These materials can be directly dispersed in water.

Other hydrophilically substituted silicone compounds include amino substituted materials. Suitable alkylamino substituted silicone compounds include those represented by the following structure (II)

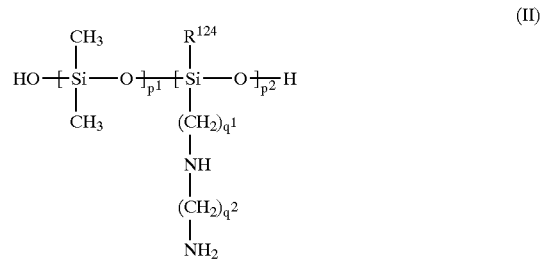

(II)

wherein $R^{124}$ is H, $CH_3$ or OH, $p^1$, $p^2$, $q^1$ and $q^2$ are integers which depend on the molecular weight, the weight average molecular weight being approximately between 5,000 and 10,000. This polymer is also known as "amodimethicone". These Amodimethicones are available, for example, from Dow Corning as SM8704C.

Suitable amino substituted silicone fluids include those represented by the formula (III)

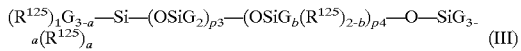
(III)

in which G is chosen from the group consisting of hydrogen, phenyl, OH, $C_1$–$C_8$ alkyl and preferably methyl; a denotes 0 or an integer from 1 to 3, and preferably equals 0; b denotes 0 or 1 and preferably equals 1; the sum $p^3+p^4$ is a number from 1 to 2,000 and preferably from 50 to 150, $p^3$ being able to denote a number from 0 to 1,999 and preferably from 49 to 149 and $p^4$ being able to denote an integer from 1 to 2,000 and preferably from 1 to 10; $R^{125}$ is a monovalent radical of formula $C_{q3}H_{2q3}L$ in which $q^3$ is an integer from 2 to 8 and L is chosen from the groups —N($R^{125}$)CH$_2$—CH$_2$—N($R^{126}$)$_2$
—N($R^{126}$)$_2$
—N($R^{126}$)$_3$X'
—N($R^{126}$)CH$_2$—CH$_2$—NR$^{126}$H$_2$X' in which $R^{126}$ is chosen from the group consisting of hydrogen, phenyl, benzyl, a saturated hydrocarbon radical, preferably an alkyl radical containing from 1 to 20 carbon atoms, and X' denotes a halide ion.

An especially preferred amino substituted silicone corresponding to formula (III) is the polymer known as "trimethylsilylamodimethicone" wherein $R^{124}$ is CH$_3$.

Other amino substituted silicone polymers useful herein include cationic amino substituted silicones represented by the formula (V):

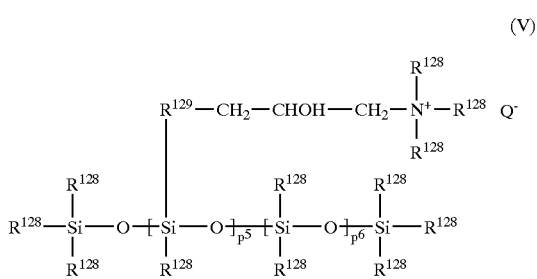
(V)

where $R^{128}$ denotes a monovalent hydrocarbon radical having from 1 to 18 carbon atoms, preferably an alkyl or alkenyl radical such as methyl; $R^{129}$ denotes a hydrocarbon radical, preferably a $C_1$–$C_{18}$ alkylene radical or a $C_1$–$C_{18}$, and more preferably $C_1$–$C_8$, alkyleneoxy radical; Q' is a halide ion, preferably chloride; $p^5$ denotes an average statistical value from 2 to 20, preferably from 2 to 8; $p^6$ denotes an average statistical value from 20 to 200, and preferably from 20 to 50. A preferred polymer of this class is available from Union Carbide under the name "UCAR SILICONE ALE 56." These materials can be directly dispersed in water.

Commercially available amino substituted silicone compounds which are useful herein include tradenames BY16-893 and BY16-907 available from Dow Corning, tradename XS69-B5476 available from General Electric, Abilquat series available from Goldschmidt, and Ultrasil series from Noveon (B.F. Goodrich).

Amino silicone polyether compounds are particularly useful herein as hydrophilically substituted silicone compounds. Amino silicone polyether compounds useful herein are those which comprise a methylpolysiloxane moiety, an amino moiety, and an polyalkoxy moiety; is water dispersible, and preferably water soluble to some extent. Without being bound by theory, it is believed that the polyalkoxy groups such as ethylene oxide groups provide good water dispersion characteristic, while the amino groups provide good conditioning characteristic as being substantive to the hair surface. The amino silicone polyether compounds for use herein will preferably have a viscosity of less than about 5000 mPa·s at 25° C., more preferably less than about 1000 mPa·s. The viscosity can be measured by means of a glass capillary viscometer as set forth in Dow Corning Corporate Test Method CTM0004, Jul. 20, 1970. Other nonvolatile silicone compounds having hair conditioning properties can also be used. Without being bound by theory, silicone compounds having lower viscosities are believed to provide faster dispersion when in contact with water.

Particularly useful amino silicone polyether compounds herein include those represented by the following structure (I):

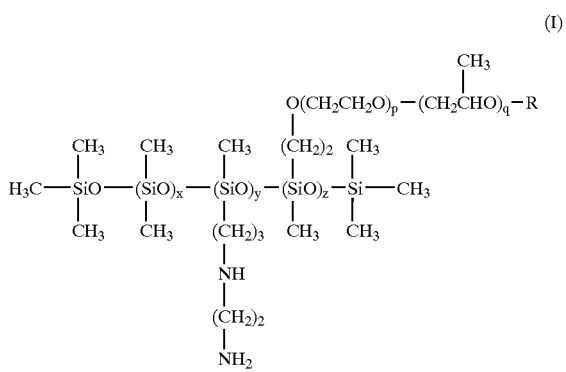
(I)

wherein none of p, q, x, y, and z are 0, but are integers that give the compound the tranparency and dispersibility as described above, preferably the preferred viscosity properties described above, and R is an alkyl of 1 to 3 carbon atoms.

Commercially available amino silicone polyether compounds that are highly preferred for use herein include those materials with tradenames: BY16-893 and BY16-907 available from Dow Corning, XS69-B5476 available from GE Toshiba Silicone, and the Ultrasil series available from BF Goodrich.

Polyalkylene Glycols

The polyalkylene glycols useful herein include those which are soluble or dispersible in water. Polyethylene glycols are preferred.

Polyalkylene glycols having a molecular weight of more than about 100 are useful herein. Useful are those having the following general formula:

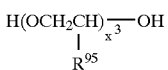

wherein $R^{95}$ is selected from the group consisting of H, methyl, and mixtures thereof. When $R^{95}$ is H, these materials are polymers of ethylene oxide, which are also known as olyethylene oxides, polyoxyethylenes, and polyethylene glycols. When $R^{95}$ is methyl, these materials are polymers of propylene oxide, which are also known as polypropylene oxides, polyoxypropylenes, and polypropylene glycols. When $R^{95}$ is methyl, it is also understood that various positional isomers of the resulting polymers can exist.

Ethylene oxide polymers are preferred in view of their generally good water solubility, dispersibility, and transparency. Polyethylene-polypropylene glycols and polyoxyethylene-polyoxypropylene copolymer polymers having good dispersibiity and transparency may also be useful. In the above structure, x3 has an average value of from about 4 to about 600, preferably from about 6 to about 120, and more preferably from about 10 to about 40. Polyethylene glycol polymers useful herein are Carbowax PEG 600 wherein $R^{95}$ equals H and x3 has an average value of about 12, available from Amerchol Inc., and Polyethylene Glycol #1000 wherein $R^{95}$ equals H and x3 has an average value of about 20 available from Kanto Chemical Co., Ltd.

Aqueous Carrier

The compositions of the present invention comprise an aqueous carrier. Aqueous carriers useful herein include water and/or water-soluble solvents. Water is useful herein. Deionized water is preferably used. Water from natural sources including mineral cations can also be used, depending on the desired characteristic of the product.

Water-soluble solvents such as lower alkyl alcohols and polyhydric alcohols are useful herein. The lower alkyl alcohols useful herein are monohydric alcohols having 1 to 6 carbons, more preferably ethanol and isopropanol. The polyhydric alcohols useful herein include propylene glycol, hexylene glycol, glycerin, propane diol, ethylene glycol, diethylene glycol, sorbitol, and other sugars which are in liquid form at ambient temperature.

Rinse Aid System

The composition of the present invention may further contain a rinse aid system for effective rinsing of the shampoo composition and soils from the hair by reducing suds, and/or reducing water hardness. The rinse aid system may be provided within the conditioning composition, or as an independent composition. When the rinse aid system is provided as an independent composition, it is preferably released in the water simultaneously with the conditioning composition.

The rinse aid system is selected from the group consisting of a pH control agent for suppressing the pH to below 6.5, a suds suppressing agent, a metal ion control agent, a crystal growth inhibitor, a dispersant polymer, a builder, and mixtures thereof. Preferably a mixture is used. Preferably a suds suppressing agent is comprised in the rinse aid system.

pH Control Agents

Inorganic and organic acids useful as pH control agents include, for example, carboxylate acids, such as citric and succinic acids, polycarboxylate acids, such as polyacrylic acid, and also acetic acid, boric acid, malonic acid, adipic acid, fumaric acid, lactic acid, glycolic acid, tartaric acid, tartronic acid, maleic acid, their derivatives and any mixtures of the foregoing.

A pH buffering agent may be used to maintain the desired pH range upon dissolving/dispersing of the composition. Materials useful as pH buffering agents include alkali metal salts of carbonates, preferably sodium bicarbonate, polycarbonates, sesquicarbonates, silicates, polysilicates, borates, metaborates, phosphates, preferably sodium phosphate such as sodium hydrogenophosphate, polyphosphate like sodium tripolyphosphate, alluminates, and mixtures thereof, and preferably are selected from alkali metal salts of carbonates, phosphates, and mixtures thereof.

Suds Suppressing Agent

Suds suppressing agents useful herein include antifoam compounds. Antifoam compounds for use herein are silica components. Preferably, these silica components are used in combination with the silicone compound described above as a conditioning agent. The term "silicone" as used herein, and in general throughout the industry, encompasses a variety of relatively high molecular weight polymers containing siloxane units and hydrocarbyl group of various types like the polyorganosiloxane oils, such as polydimethyl-siloxane, dispersions or emulsions of polyorganosiloxane oils or resins, and combinations of polyorganosiloxane with silica particles wherein the polyorganosiloxane is chemisorbed or fused onto the silica. Silica components useful for suds suppressers are well known in the art and are, for example, disclosed in U.S. Pat. No. 4,265,779, issued May 5, 1981 to Gandolfo et al and European Patent Application No. 89307851.9, published Feb. 7, 1990, by Starch, M. S. Other silicone suds suppressers are disclosed in U.S. Pat. No. 3,455,839 which relates to compositions and processes for defoaming aqueous solutions by incorporating therein small amounts of polydimethylsiloxane fluids. Mixtures of silicone and silanated silica are described, for instance, in German Patent Application DOS 2,124,526. Examples of suitable silicone antifoam compounds are the combinations of polyorganosiloxane with silica particles commercially available from Dow Corning, SE39 available from Wacker Chemie, and TSA775 available from General Electric.

Other antifoam compounds include the monocarboxylic fatty acids and soluble salts thereof, such as those having hydrocarbyl chains of 10 to about 24 carbon atoms, preferably 12 to 18 carbon atoms like the tallow amphopolycarboxyglycinate commercially available under the trade name TAPAC. Suitable salts include the alkali metal salts such as sodium, potassium, and lithium salts, and ammonium and alkanolammonium salts.

Other suitable antifoam compounds include, for example, high molecular weight hydrocarbons such as paraffin, light petroleum, odorless hydrocarbons, fatty esters (e.g. fatty acid triglycerides, glyceryl derivatives, polysorbates), fatty acid esters of monovalent alcohols, aliphatic $C_{18}$–$C_{40}$ ketones (e.g. stearone) N-alkylated amino triazines such as tri- to hexa-alkylmelamines or di- to tetra alkyldiamine chlortriazines formed as products of cyanuric chloride with two or three moles of a primary or secondary amine containing 1 to 24 carbon atoms, propylene oxide, bis stearic acid amide and monostearyl phosphates such as monostearyl alcohol phosphate ester and monostearyl di-alkali metal (e.g., K, Na, and Li) phosphates and phosphate esters, quaternary ammonium compounds, di-alkyl quaternary compounds, poly functionalised quaternary compounds, and nonionic polyhydroxyl derivatives.

Copolymers of ethylene oxide and propylene oxide, particularly the mixed ethoxylated/propoxylated fatty alcohols with an alkyl chain length of from 10 to 16 carbon atoms, a degree of ethoxylation of from 3 to 30 and a degree of propoxylation of from 1 to 10, are also suitable antifoam compounds for use herein.

Other suds suppressers useful herein comprise secondary $C_6$–$C_{16}$ alkyl alcohols having a $C_1$–$C_{16}$ chain like the 2-Hexyldecanol commercially available under the trade name ISOFOL16, 2-Octyldodecanol commercially available under the tradename ISOFOL20, and 2-butyl octanol, which is available under the trademark ISOFOL 12 from Condea. A preferred alcohol is 2-butyl octanol, which is available from Condea under the trademark ISOFOL 12. Mixtures of secondary alcohols are available under the trademark ISALCHEM 123 from Enichem.

Metal Ion Control Agents

Heavy metal ion (HMI) sequestrants which act to sequester (chelate) heavy metal ions are useful herein. These components may have calcium and magnesium chelation capacity, but preferentially they bind heavy metal ions such as iron, manganese and copper. These compounds are even more desired when the water is a tap water of low quality and consequently that which comprises a high level of HMI.

Heavy metal ion sequestrants, which are acidic in nature, having for example phosphonic acid or carboxylic acid functionalities, may be present either in their acid form or as a complex/salt with a suitable counter cation such as an alkali or alkaline metal ion, ammonium, or substituted ammonium ion, or any mixtures thereof.

Suitable heavy metal ion sequestrants for use herein include the organo aminophosphonates, such as the amino alkylene poly (alkylene phosphonates) and nitrilo trimethylene phosphonates. Preferred organo aminophosphonates are diethylene triamine penta (methylene phosphonate) and hexamethylene diamine tetra (methylene phosphonate).

Other suitable heavy metal ion sequestrants for use herein include nitrilotriacetic acid and polyaminocarboxylic acids such as ethylenediaminotetracetic acid, ethylenetriamine pentacetic acid, or ethylenediamine disuccinic acid. A further suitable material is ethylenediamine-N,N'-disuccinic acid (EDDS), most preferably present in the form of its S,S isomer, which is preferred for its biodegradability profile. Still other suitable heavy metal ion sequestrants for use herein are iminodiacetic acid derivatives such as 2-hydroxyethyl diacetic acid or glyceryl imino diacetic acid.

Crystal Growth Inhibitors

Non-limiting examples of carboxylic compounds which serve as crystal growth inhibitors include carboxylic compounds such as glycolic acid, phytic acid, polycarboxylic acids, polymers and co-polymers of carboxylic acids and polycarboxylic acids, and mixtures thereof. The inhibitors may be in the acid or salt form. Preferably the polycarboxylic acids comprise materials having at least two carboxylic acid radicals which are separated by not more than two carbon atoms (e.g., methylene units). Further suitable polycarboxylates include ether hydroxypolycarboxylates, polyacrylate polymers, copolymers of maleic anhydride and the ethylene ether or vinyl methyl ethers of acrylic acid. Copolymers of 1,3,5-trihydroxybenzene, 2, 4, 6-trisulphonic acid, and carboxymethyloxysuccinic acid are also useful. Alkali metal salts of polyacetic acids, for example, ethylenediamine tetraacetic acid and nitrilotriacetic acid, and the alkali metal salts of polycarboxylates, for example, mellitic acid, succinic acid, oxydisuccinic acid, polymaleic acid, benzene 1,3,5-tricarboxylic acid, carboxymethyloxysuccinic acid, are suitable for use in the present invention as crystal growth inhibitors.

The polymers and copolymers which are useful as crystal growth inhibitors have a molecular weight which is preferably greater than about 500 daltons to about 100,000 daltons, more preferably to about 50,000 daltons.

Examples of commercially available materials for use as crystal growth inhibitors include, polyacrylate polymers Good-Rite® ex BF Goodrich, Acrysol® ex Rohm & Haas, Sokalan® ex BASF, and Norasol® ex Norso Haas. Preferred are the Norasol® polyacrylate polymers, more preferred are Norasol® 410N (MW 10,000) and Norasol® 440N (MW 4000) which is an amino phosphonic acid modified polyacrylate polymer, and also more preferred is the acid form of this modified polymer sold as Norasol® QR 784 (MW 4000) ex Norso-Haas.

Polycarboxylate crystal growth inhibitors include citrates, e.g., citric acid and soluble salts thereof (particularly sodium salt), 3,3-dicarboxy-4-oxa-1,6-hexanedioates and related compounds further disclosed in U.S. Pat. No. 4,566,984 incorporated herein by reference, $C_5$–$C_{20}$ alkyl, $C_5$–$C_{20}$ alkenyl succinic acid and salts thereof, of which dodecenyl succinate, lauryl succinate, myristyl succinate, palmityl succinate, 2-dodecenylsuccinate, 2-pentadecenyl succinate, are non-limiting examples.

Organic diphosphonic acid are also suitable for use as crystal growth inhibitors. For the purposes of the present invention the term "organic diphosphonic acid" is defined as "an organo-diphosphonic acid or salt which does not comprise a nitrogen atom". Preferred organic diphosphonic acids include $C_1$–$C_4$ diphosphonic acid, preferably $C_2$ diphosphonic acid selected from the group consisting of ethylene diphosphonic acid, α-hydroxy-2 phenyl ethyl diphosphonic acid, methylene diphosphonic acid, vinylidene-1,1-diphosphonic acid, 1,2-dihydroxyethane-1,1-diphosphonic acid, hydroxy-ethane 1,1 diphosphonic acid, the salts thereof, and mixtures thereof. More preferred is hydroxyethane-1,1-diphosphonic acid (HEDP).

Still useful herein as crystal growth inhibitor are the organic monophosphonic acid. Organo monophosphonic acid or one of its salts or complexes is also suitable for use herein as a crystal growth inhibitor. By organo monophosphonic acid it is meant herein an organo monophosphonic acid which does not contain nitrogen as part of its chemical structure. This definition therefore excludes the organo aminophosphonates, which however may be included in compositions of the invention as heavy metal ion sequestrants.

The organo monophosphonic acid component may be present in its acid form or in the form of one of its salts or complexes with a suitable counter cation. Preferably any salts/complexes are water soluble, with the alkali metal and alkaline earth metal salts/complexes being especially preferred.

A preferred organo-monophosphonic acid is 2-phosphonobutane-1,2,4-tricarboxylic acid commercially available from Bayer under the trade name of Bayhibit.

Dispersant Polymers

Suitable polymeric dispersing agents include polymeric polycarboxylates and polyethylene glycols, although others known in the art can also be used. It is believed, though it is not intended to be limited by theory, that polymeric dispersing agents enhance overall rinsing performance.

Polymeric polycarboxylate materials can be prepared by polymerizing or copolymerizing suitable unsaturated monomers, preferably in their acid form. Unsaturated monomeric acids that can be polymerized to form suitable polymeric polycarboxylates include acrylic acid, maleic acid (or maleic anhydride), fumaric acid, itaconic acid, aconitic acid, mesaconic acid, citraconic acid and methylenemalonic acid. The presence in the polymeric polycarboxylates herein of monomeric segments, containing no carboxylate radicals such as vinylmethyl ether, styrene, ethylene, etc. is suitable provided that such segments do not constitute more than about 40% by weight.

Particularly suitable polymeric polycarboxylates can be derived from acrylic acid. Such acrylic acid-based polymers which are useful herein are the water-soluble salts of polymerized acrylic acid. The average molecular weight of such polymers in the acid form preferably ranges from about 2,000 to 10,000, more preferably from about 4,000 to 7,000 and most preferably from about 4,000 to 5,000. Water-soluble salts of such acrylic acid polymers can include, for example, the alkali metal, ammonium and substituted ammonium salts. Soluble polymers of this type are known materials.

Acrylic/maleic-based copolymers may also be used as a preferred component of the dispersing/anti-redeposition agent. Such materials include the water-soluble salts of copolymers of acrylic acid and maleic acid. The average molecular weight of such copolymers in the acid form preferably ranges from about 2,000 to 100,000, more preferably from about 5,000 to 75,000, most preferably from about 7,000 to 65,000. The ratio of acrylate to maleate segments in such copolymers will generally range from about 30:1 to about 1:1, more preferably from about 10:1 to 2:1. Water-soluble salts of such acrylic acid/maleic acid copolymers can include, for example, the alkali metal, ammonium and substituted ammonium salts. Soluble acrylate/maleate copolymers of this type are known materials which are described in European Patent Application No. 66915, published Dec. 15, 1982, as well as in EP 193,360, published Sep. 3, 1986, which also describes such polymers comprising hydroxypropylacrylate. Still other useful dispersing agents include the maleic/acrylic/vinyl alcohol terpolymers. Such materials are also disclosed in EP 193,360, including, for example, the 45/45110 terpolymer of acrylic/maleic/vinyl alcohol.

Polyaspartate and polyglutamate dispersing agents may also be used, especially in conjunction with zeolite builders. Dispersing agents such as polyaspartate preferably have a molecular weight (avg.) of about 10,000.

A group of preferred clay soil removal/anti-redeposition agents are the cationic compounds disclosed in European Patent Application 111,965, Oh and Gosselink, published Jun. 27, 1984. Other clay soil removal/antiredeposition agents which can be used include the ethoxylated amine polymers disclosed in European Patent Application 111,984, Gosselink, published Jun. 27, 1984; the zwitterionic polymers disclosed in European Patent Application 112,592, Gosselink, published Jul. 4, 1984; and the amine oxides disclosed in U.S. Pat. No. 4,548,744, Connor, issued Oct. 22, 1985. Other clay soil removal and/or anti-redeposition agents known in the art can also be utilized in the compositions herein. Another type of preferred anti-redeposition agent includes the carboxymethylcellulose (CMC) materials.

Builders

The rinse aid used in the compositions of the present invention may also comprise builders to assist in controlling mineral hardness. Inorganic as well as organic builders can be used.

Inorganic or P-containing builders include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates. However, non-phosphate builders are required in some locales. Importantly, the compositions herein function surprisingly well even in the presence of the so-called "weak" builders (as compared with phosphates) such as citrate, or in the so-called "underbuilt" situation that may occur with zeolite or layered silicate builders.

Examples of silicate builders are the alkali metal silicates, particularly those having a $SiO_2:Na_2O$ ratio in the range 1.6:1 to 3.2:1 and layered silicates, such as the layered sodium silicates; NaSKS-6 is the trademark for a crystalline layered silicate marketed by Hoechst (commonly abbreviated herein as "SKS-6"). Unlike zeolite builders, the Na-SKS-6 silicate builder does not contain aluminum. Na-SKS-6 has the delta-$Na_2$ $SiO_5$ morphology form of layered silicate. SKS-6 is a highly preferred layered silicate for use herein, but other such layered silicates, such as those having the general formula $NaMSi_xO_{2x+1}.yH_2O$ wherein M is sodium or hydrogen, x is a number from 1.9 to 4, preferably 2, and y is a number from 0 to 20, preferably 0 can be used herein. Various other layered silicates from Hoechst include NaSKS-5, NaSKS-7 and NaSKS-11, as the alpha, beta and gamma forms. As noted above, the delta-$Na_2$ $SiO_5$ (NaSKS-6 form) is most preferred for use herein.

Aluminosilicate builders are useful in the present invention. Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al, issued Oct. 12, 1976. Preferred synthetic crystalline aluminosilicate ion exchange materials useful herein are available under the designations Zeolite A, Zeolite P (B), Zeolite MAP and Zeolite X. Particularly preferred is Zeolite A. Dehydrated zeolites may also be used herein. Preferably, the aluminosilicate has a particle size of about 0.1–10 microns in diameter.

Citrate builders, e.g., citric acid and soluble salts thereof (particularly sodium salt), are polycarboxylate builders of particular importance for liquid detergent formulations due to their availability from renewable resources and their biodegradability.

Also suitable in the compositions of the present invention are the 3,3-dicarboxy-4-oxa-1,6-hexanedioates and the related compounds. Useful succinic acid builders include the $C_5$–$C_{20}$ alkyl and alkenyl succinic acids and salts thereof. A particularly preferred compound of this type is dodecenylsuccinic acid. Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group.

Fatty acids, e.g., C12–C18 monocarboxylic acids, can also be incorporated into the compositions alone, or in combination with the aforesaid builders, especially citrate and/or the succinate builders, to provide additional builder activity.

In situations where phosphorus-based builders can be used, the various alkali metal phosphates such as the well-known sodium tripolyphosphates, sodium pyrophosphate and sodium orthophosphate can be used. Phosphonate builders such as ethane-1-hydroxy-1,1-diphosphonate and other known phosphonates can also be used.

Additional Components

A wide variety of other additional components can be formulated into the present compositions. These include: other conditioning agents such as hydrolysed collagen with tradename Peptein 2000 available from Hormel, vitamin E with tradename Emix-d available from Eisai, panthenol available from Roche, panthenyl ethyl ether available from Roche, hydrolysed keratin, proteins, plant extracts, and nutrients; preservatives such as methyl chloroisothiazolinone, methyl isothiazolinone, benzyl alcohol, methyl paraben, propyl paraben and imidazolidinyl urea; thickeners such as hydroxyethyl cellulose, hydroxypropyl methylcellulose, polyacrylamide, and cetyl hydroxyethyl cellulose; salts, in general, such as potassium acetate and sodium chloride; coloring agents, such as any of the FD&C or D&C dyes; perfumes; ultraviolet and infrared screening and absorbing agents such as octyl salicylate; antidandruff agents such as zinc pyridinethione; and optical brighteners, for example polystyrylstilbenes, triazinstilbenes, hydroxycoumarins, aminocoumarins, triazoles, pyrazolines, oxazoles, pyrenes, porphyrins, imidazoles, and mixtures thereof.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or CTFA name, or otherwise defined below.

Examples 1 through 16 are hair conditioning compositions of the present invention which are used by dispersing in water to make a treated water and applying the treated water to the shampooed hair.

Compositions of Examples 1 through 6

| Components | Ex. 1 | Ex. 2 | Ex. 3 | Ex. 4 | Ex. 5 | Ex. 6 |
|---|---|---|---|---|---|---|
| Cetyl Trimethyl Ammonium Chloride *1 | 1.5 | | | | 3.0 | 1.5 |
| Stearyl Trimethyl Ammonium Chloride *2 | | 2.0 | | | | |
| Palmitamidopropyl Trimethyl Ammonium Chloride *3 | | | 3.0 | | | |
| PEG-15 Stearmonium Chloride *4 | | | | 2.0 | | |
| Polyquaternium-10 *5 | 1.5 | | 1.0 | | | |
| Polyquaternium-4 *6 | | 2.0 | | 2.0 | 3.0 | |
| Polyquaternium-7 *7 | | | | | | 1.5 |
| Polyethylene Glycol 600 *8 | | | | | | 1.0 |
| Suds Suppressant *14 | 0.15 | 0.15 | | | 0.15 | 0.15 |
| Thickener *15 | 0.45 | 0.20 | 0.55 | 0.30 | | 0.6 |
| Preservative | 0.40 | 0.40 | 0.40 | 0.40 | 0.40 | 0.40 |
| Water | to make 100% | | | | | |

Compositions of Examples 7 through 12

| Components | Ex. 7 | Ex. 8 | Ex. 9 | Ex. 10 | Ex. 11 | Ex. 12 |
|---|---|---|---|---|---|---|
| Cetyl Trimethyl Ammonium Chloride *1 | | 1.5 | | | | 2.5 |
| Stearyl Trimethyl Ammonium Chloride *2 | 1.0 | | 1.0 | | | |
| Palmitamidopropyl Trimethyl Ammonium Chloride *3 | | | | 2.5 | | |
| PEG-15 Stearmonium Chloride *4 | | | | | 2.0 | |
| Polyquaternium-10 *5 | 2.0 | 1.5 | 2.0 | | 2.0 | |
| Polyquaternium-4 *6 | | | | 1.5 | | 1.0 |
| Polyethylene Glycol 1000 *9 | 3.0 | | | | | |
| Amino Silicone A *10 | | 1.0 | | | | 1.5 |
| Amino Silicone B *11 | | | 1.5 | | | |
| Amino Silicone C *12 | | | | 1.0 | | |
| Quaternium-80 *13 | | | | | 0.50 | |
| Suds Suppressant *14 | 0.15 | 0.15 | 0.15 | | | 0.15 |
| Thickener *15 | 0.20 | 0.45 | 0.25 | 0.50 | 0.20 | 0.55 |
| Preservative | 0.40 | 0.40 | 0.40 | 0.40 | 0.40 | 0.40 |
| Water | to make 100% | | | | | |

Compositions of Examples 13 through 16

| Components | Ex. 13 | Ex. 14 | Ex. 15 | Ex. 16 |
|---|---|---|---|---|
| Cetyl Trimethyl Ammonium Chloride *1 | 1.5 | | | |
| Stearyl Trimethyl Ammonium Chloride *2 | | 1.5 | | |
| Palmitamidopropyl Trimethyl Ammonium Chloride *3 | | | 3.0 | |
| PEG-15 Stearmonium Chloride *4 | | | | 1.5 |
| Polyquaternium-10 *5 | 0.5 | | | |
| Polyquaternium-4 *6 | | 1.5 | | |
| Polyquaternium-7 *7 | 1.5 | 1.0 | | 2.0 |
| Polyethylene Glycol 600 *8 | 1.0 | | 3.0 | |
| Polyethylene Glycol 1000 *9 | | 2.0 | | 1.0 |
| Amino Silicone A *10 | 1.0 | | | |
| Amino Silicone B *11 | | 1.0 | | |
| Amino Silicone C *12 | | | 2.0 | |
| Quaternium-80 *13 | | | | 1.5 |
| Suds Suppressant *14 | 0.15 | 0.15 | | |
| Thickener *15 | 0.45 | 0.50 | 0.40 | 0.25 |
| Preservative | 0.40 | 0.40 | 0.40 | 0.40 |
| Water | to make 100% | | | |

Definitions of Components
*1 Cetyl Trimethyl Ammonium Chloride: CTAC 30KC from KCl
*2 Stearyl Trimethyl Ammonium Chloride: Arquad 18/50 from Akzo Nobel
*3 Palmitamidopropyl Trimethyl Ammonium Chloride: Varisoft PATC from Goldschmidt
*4 PEG-15 Stearmonium Chloride: Ethoquad 18/25 from Akzo Nobel
*5 Polyquaternium-10: Polymer LR-400 from Amerchol
*6 Polyquaternium-4: Celquat L200 from National Starch & Chemicals
*7 Polyquaternium-7: Salcare SC11 from Ciba Specialty Chemicals
*8 Polyethylene Glycol 600: Carbowax PEG 600 from Amerchol
*9 Polyethylene Glycol 1000: Polyethylene Glycol #1000 from Kanto Chemical Co., Inc.
*10 Amino Silicone A: BY16-893 Dow Corning Silicones
*11 Amino Silicone B: XS69-B5476 from General Electric Silicones
*12 Amino Silicone C: Ultrasil A-100 from BFGoodrich Specialty Chemicals
*13 Quaternium-80: Abilquat 3474 from Goldschmidt
*14 Suds Suppressant: TSA775 from General Electric Silicones
*15 Thickener: Hydroxyethyl Cellulose from Hercules Chemicals Method of Preparation The compositions of Examples 1–16 as shown above can be prepared by any conventional method.

Examples 1–16 can be made by mixing the components, as necessary with agitation and elevated temperature. The resulting compositions provide a liquid form. The liquid form composition can be filled into a bottle having a pump providing unit dosage amount of the liquid. Unit dosage amount of this liquid form composition can be filled into a sachet made of plastic film which does not interact with the composition.

The embodiments disclosed and represented by the previous examples have many advantages. All Examples 1–16 have a turbidity of less than 200 NTU. When released in water to make a treated water, all Examples 1–16 immediately disperse after mixing with the hand, and provide treated water having a turbidity of less than 100 NTU.

Further, upon and after application to the shampooed hair, they can provide conditioning benefit such as soft and smooth hair feel, easy wet and dry hair coming, and shine.

It is understood that the examples and embodiments described herein are for illustrative purposes only and that various modifications or changes in light thereof will be suggested to one skilled in the art without departing from its spirit and scope.

What is claimed is:

1. A method of conditioning the hair comprising the steps of:
   (a) applying a shampoo composition comprising a detersive surfactant to the hair;
   (b) providing a treated water having a concentrated by weight of from 0.001% to 2% of a conditioning agent by dispersing a conditioning composition comprising:
      (1) 0.01% to 50% by weight of the conditioning agent selected from the group consisting of mono long chain ammonium compounds, cationic surfactants, cationic polymers, silicone compounds, polyalkylene glycols and mixtures thereof; and (2) an aqueous carrier;
(3) wherein the conditioning composition has a turbidity of no more than 200 NTU, and the treated water has a turbidity of no more than 100 NTU; and (c) rinsing the hair treated with water;
wherein the steps (a) and (b) may be reversed.

2. The conditioning composition according to claim 1 comprising from about 1% to about 20% of the conditioning agent.

3. The conditioning composition of claim 1 comprising from about 1% to about 10% of a mono long-chain ammonium compound or hydrophilically substituted cationic surfactant and from about 1% to about 10% of a cationic polymer.

4. The conditioning composition of claim 1 comprising from about 0.01% to about 20% of a hydrophilically substituted silicone compound having substitute groups selected from the group consisting of alkoxy groups, amino groups, quaternary amino groups, and mixtures thereof.

5. The conditioning composition of claim 1 further comprising a rinse aid system selected from the group consisting of a pH control agent for suppressing the pH to below 6.5, a suds suppressing agent, a metal ion control agent, a crystal growth inhibitor, a dispersant polymer, a builder, and mixtures thereof.

6. The conditioning composition of claim 5 wherein the rinse aid system comprises a suds suppressing agent.

* * * * *